United States Patent [19]

Cramer

[11] 4,380,292

[45] Apr. 19, 1983

[54] PARENTERAL NEEDLE RECEPTACLE

[76] Inventor: Kathleen J. Cramer, 4240 Crooked Tree Apt. #7, Wyoming, Mich. 49509

[21] Appl. No.: 242,345

[22] Filed: Mar. 10, 1981

[51] Int. Cl.³ .................. B65D 85/24; B65F 7/00; A61C 17/02; B65D 81/00
[52] U.S. Cl. .................. 206/366; 206/63.5; 206/370; 206/813; 206/818
[58] Field of Search .......... 206/205, 366, 45.34, 206/523, 818, 813, 63.5; 223/109 R

[56] References Cited

U.S. PATENT DOCUMENTS

| | | |
|---|---|---|
| Re. 26,426 | 7/1968 | DeRemer et al. |
| 271,828 | 2/1883 | Fountain . |
| 1,349,232 | 8/1920 | Stanko . |
| 1,725,999 | 8/1929 | Ryder ................ 223/109 R |
| 2,087,372 | 7/1920 | Crawford ............ 223/109 R |
| 2,124,352 | 7/1938 | Patten . |
| 2,264,313 | 12/1941 | Humphrey . |
| 2,756,895 | 7/1956 | Enders . |
| 2,971,640 | 2/1961 | Snelling . |
| 3,367,483 | 2/1968 | Studen ................ 206/45.34 |
| 3,561,146 | 2/1971 | Dembar ............. 206/45.34 |
| 3,727,658 | 4/1973 | Eldridge, Jr. . |
| 3,819,039 | 6/1974 | Erickson . |
| 3,876,067 | 4/1975 | Schwarz . |
| 3,944,069 | 3/1976 | Eldrige, Jr. . |
| 4,008,802 | 2/1977 | Freitag . |
| 4,078,701 | 3/1978 | Clubb . |
| 4,151,913 | 5/1979 | Freitag . |
| 4,182,448 | 1/1980 | Huck et al. . |
| 4,195,729 | 4/1980 | Macken .............. 206/45.34 |

Primary Examiner—William T. Dixson, Jr.
Attorney, Agent, or Firm—Price, Heneveld, Huizenga & Cooper

[57] ABSTRACT

A parenteral needle receptacle including a base, a case releasably mounted on the base, and a block releasably retained therebetween. The case includes an opening through which needles can be inserted into the block. In the preferred embodiment, magnets are secured within or on the base so that the receptacle can be mounted on a ferrous surface. An alternative embodiment of the receptacle includes a small, single-use case, a needle-receiving block positioned therein, and two-sided adhesive tape secured to the case so that the case can be mounted on an object.

17 Claims, 6 Drawing Figures

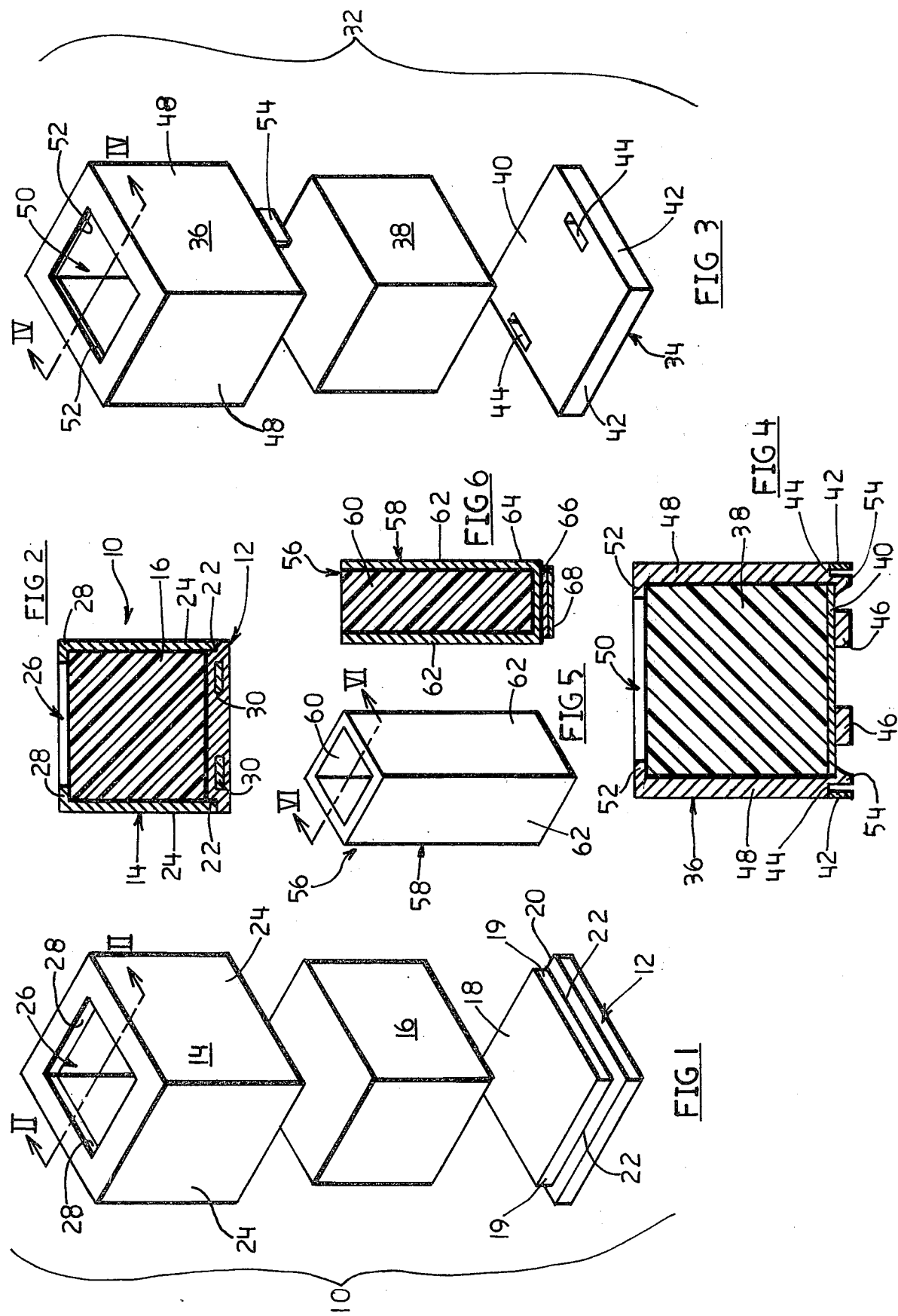

PARENTERAL NEEDLE RECEPTACLE

1. Field of the Invention

The present invention relates to disposal of used hypodermic, intramuscular, intravenous and suture needles hereinafter referred to collectively as parenteral needles.

2. Description of the Prior Art

Certain forms of hepatitis are transmitted by blood. Hepatitis is often transmitted when a health care worker accidentally punctures himself or herself with a used parenteral needle.

Currently, approximately 7,000 to 10,000 health care workers contract hepatitis annually. A significant number of these cases occur when the worker is accidentally punctured with a used parenteral needle.

The consequences of contracting hepatitis are extremely serious. First, the person contracting the disease must miss approximately three to fifteen weeks of work due to a prolonged recovery period. Furthermore, four to six percent of those contracting hepatitis remain antigen positive after recovery and, consequently, cannot work in the same profession. Finally, some individuals contracting hepatitis will unavoidably die as a result of the disease.

In addition to the risk of contracting hepatitis, other infections may result from an accidental puncture with a contaminated needle. Such possible infections include syphilis as well as other diseases.

Although the consequences are severe, relatively little has been done to safely dispose of used parenteral needles to reduce the possibility of transmitting hepatitis. Health care workers might be punctured by these needles at any number of times. First, a worker might be punctured when he attempts to remove a needle from a syringe or IV tubing. Second, a puncture may occur when he attempts to reinsert the needle into a protective sheath before disposing of the entire assembly. Finally, workers may be punctured by loose needles which have been thrown improperly into a waste container.

Although syringe needle collection boxes have been previously constructed, they are not without their disadvantages. For example, one prior artisan constructed a box having a disinfectant filling and a cover plate having a grid of square openings through which needles may be inserted. Each of the square openings is designed to lockingly receive the base of a needle thereby retaining the needle within the box. An example of this type of construction may be found in U.S. Pat. No. 3,876,067. However, this box is expensive, is permanently closed and has a needle retaining grid. Once filled with needles, it must be disposed of, thereby increasing the expense of needle disposal. Second, the user must hold the case with his free hand and, consequently, may puncture his free hand if he accidentally misses the case while inserting the needle. Third, the grid-like cover restricts use of the case to a limited range of needle sizes. Finally, the grid-like retaining structure requires a so-called "one-way" parenteral needle which is easily detached from the syringe.

Although a number of prior art devices have been developed for protectively securing surgical sharps and surgical needles prior to disposal, these devices are not readily adaptable to parenteral needles because they lack the means for receiving the relatively long shaft of the syringe needle. Examples of such recptacles may be found in U.S. Pat. Nos. 4,182,448; 4,151,913; 4,008,802; 3,944,069; and 3,727,658.

SUMMARY OF THE INVENTION

These problems are solved in the present invention which comprises a case designed for repeated use and a disposable needle receiving block releasably retained therein into which needles may be inserted. The block may be periodically discarded without having to discard the entire assembly. The opening in the case exposing the disposable core is preferably relatively large so that the receptacle can accommodate a large number of needles of any of a variety of diameters. Finally, the receptacle preferably includes means for mounting the case on another object, such as an emergency room "crash cart" or a hospital bed headboard. Consequently, one using the receptacle does not have to hold it in his free hand. This reduces the possibility of puncturing himself.

These and other objects, advantages, and features of the invention will be more fully understood and appreciated by reference to the written specification and appended drawings.

BRIEF DESCRIPTION OF THE DRAWINGS

FIG. 1 is a perspective exploded view of the parenteral needle receptacle;

FIG. 2 is a cross-sectional view taken along plane II—II in FIG. 1 with the receptacle assembled;

FIG. 3 is a perspective exploded view of an alternative embodiment of the parenteral needle receptacle;

FIG. 4 is a cross-sectional view taken along plane IV—IV in FIG. 3 with the alternative receptacle assembled;

FIG. 5 is a perspective view of yet another alternative embodiment of the receptacle; and FIG. 6 is a cross-sectional view taken along plane VI—VI in FIG. 5.

DESCRIPTION OF THE PREFERRED EMBODIMENT

Referring specifically to FIGS. 1 and 2, receptacle 10 generally comprises base 12, case 14, and foam block 16 releasably retained therebetween. Base 12 includes magnets 30 therein which facilitate positioning receptacle 10 on a crash cart or the like. A user inserts the pointed ends of needles into foam block 16. When filled, block 16 can be removed by separating base 12 from case 14 and dumping block 16 and its needles out of case 14. Base 12 is generally square when viewed from above and includes platform 18 which is also generally square. Platform 18 is somewhat smaller than and extends upwardly from lower portion 20 of base 12 so that a recess 22 is formed by case 14 surrounding platform 18. Base 12 is preferably fabricated from a sufficiently hard plastic to resist penetration by a parenteral needle. Consequently, needles inserted into the receptacle cannot be accidentally pushed through base 12.

Block 16 of the preferred embodiment is generally cube-shaped with each of its faces approximating the size of platform 18. Therefore, block 16 may be positioned on platform 18 with any of its surfaces facing upwardly. Preferably, each edge of block 16 is at least four inches long so that the receptacle can accommodate a large variety of needle lengths. The preferable material for block 16 is styrofoam so that needles may be readily inserted into block 16 and frictionally retained therein.

Case 14 is also generally cube-shaped having four outer walls 24, each of which is generally square. Opening 26 is defined by retaining ridge 28 which extends inwardly from outer walls 24. Ridge 28 prevents block 16 from traveling upwardly through opening 26. Preferably, case 14 is fabricated from a relatively hard plastic so that the case resists puncturing by needles inserted into receptacle 10.

Bar magnets 30 are encased within base 12 so that receptcle 10 may be mounted on any ferrous surface. Preferably, magnets 30 are completely encapsulated which facilitates the cleaning of base 12.

The receptacle is assembled by first positioning block 16 on platform 18. Second, case 14 is oriented so that opening 26 faces upwardly, and is then slid downwardly over block 16 into engagement with platform 18. The inner surfaces of outer walls 24 frictionally engage the outer walls 19 of platform 18 so that case 14 is secured on base 12 through a force fit. Consequently, the receptacle may be repeatedly assembled and disassembled as necessary to reorient or dispose of block 16.

An alternative embodiment 32 of the parenteral needle receptacle is shown in FIGS. 3 and 4. Base 34 is generally square when viewed from above and generally comprises platform 40 supported by four downwardly depending runners 42. Slots 44 extend through platform 40 near opposite edges thereof. Slots 44 are substantially adjacent runners 42 so that the inner surface of runner 42 forms one of the walls defining slot 44. Bar magnets 46 are secured to the undersurface of platform 40 so that the base may be mounted on a ferrous object, such as an emergency room crash cart.

Case 36 is generally cube-shaped having four generally square outer walls 48. Opening 50 is defined by retaining ridge 52 which extends inwardly from outer walls 48. Ridge 52 prevents block 38 from passing upwardly through opening 50.

Barbs 54 extend downwardly from opposite outer walls 48 and extend into slots 44 when receptacle 32 is assembled (FIG. 4). Barbs 54 engage the undersurface of platform 40 to securely retain case 36 on base 34. When case 36 is to be removed from base 34, barbs 54 are flexed outwardly, or away from each other, so that they disengage the undersurface of platform 40 and may slide upwardly through slots 44. As in the previous embodiment, both base 34 and case 36 are fabricated from a hard plastic so that both of these elements resist penetration by needles.

Block 38 which is generally cube-shaped is trapped within case 36 between platform 40 and retaining ridge 52 when receptacle 32 is assembled. Because block 38 is cube-shaped, it may be positioned within case 36 with any of its six faces adjacent opening 50. Styrofoam is preferably used to construct block 38 so that needles can be readily inserted into the block and frictionally held therein. Block 38 preferably measures at least four inches on each edge so that the block is capable of accommodating a large variety of needle sizes.

Yet another alternative embodiment 56 of the needle receptacle is shown in FIGS. 5 and 6. Receptacle 56 is intended for a single use, for example disposal of a single IV needle or a small number of suture needles.

Generally, receptacle 56 comprises case 58 and block 60 positioned therein. Case 58 includes four generally rectangular outer walls 62 and an integrally molded bottom 64. Block 60 is positioned within and substantially fills case 58. Again, block 60 is preferably fabricated from a material capable of receiving the used needle and securing same therein. Case 58 is preferably made of a hard plastic, but because the case is disposable and intended for a single use, the plastic may be relatively inexpensive.

Two-sided tape 66 is secured to bottom 64 and protectively covered using cover strip 68. Receptacle 56 may be mounted on an object by removing cover strip 68 from two-sided tape 66 exposing an adhesive surface and pushing tape 66 against the object.

Although all of the receptacles disclosed herein are generally square in cross section, it is understood that the structure could be adapted to any shape case, for example, having a circular, triangular, hexagonal or other cross section.

OPERATION

The first and second embodiments of the receptacle might be kept in a hospital emergency room with the other emergency equipment. When an injured person is brought into the emergency room, one of the health care workers mounts the parenteral needle receptacle on the crash cart by placing base 12 adjacent a ferrous portion thereof. The attraction between magnets 30 and the ferrous portion of the crash cart secures the receptacle in place.

As IV needles and other parenteral needles are withdrawn from the patient, they are immediately inserted into block 16 through opening 26. Each needle is inserted until either its tip engages platform 18 or its hilt is substantially flush with the exposed surface of block 16. Because the receptacle need not be held, it is unlikely that one inserting a needle into block 16 will puncture his hand if he should accidentally miss the receptacle.

Periodically, generally after each patient use, the needles within the receptacles are withdrawn and properly disposed of. Case 14 is then removed from base 12 and block 16 is withdrawn from case 14. Block 16 is then reoriented so that a previously unexposed surface faces upwardly against opening 26. Consequently each block may be used six times, once for each face, before it need be discarded. Case 14 is then reseated on base 12 so that the receptacle is ready for its next use.

Of course, it is understood that the receptacle may be used in other applications, particularly in doctors' offices, clinics, or other places where the disposal of parenteral needles is required.

The third described embodiment is intended for single use applications, for example with IV or transfusion needles. When the needle is inserted into the patient, cover strip 68 is removed from two-sided tape 66 and the single use receptacle 56 is secured to a nearby object, for example the IV pole or the bed headboard. Consequently, the receptacle is conveniently nearby when the needle is later withdrawn, and the withdrawn needle may be immediately inserted into block 60. Receptacle 56 is then detached from the object to which it is attached and discarded with the needle therein.

Of course, it is understood that the above merely preferred embodiments of the invention and that various changes and alterations can be made without departing from the spirit and broader aspects of the invention as set forth in the appended claims, which are to be interpreted in accordance with the principles of patent law, including the doctrine of equivalents.

The embodiments of the invention in which an exclusive property or privilege is claimed are defined as follows:

1. A parenteral needle receptacle comprising:
a base;
a case releasably mounted on said base, said case having walls defining a first open end adjacent said base and also having a second open end opposite to and smaller than said first open end;
means operatively connected to at least one of said base and said case for mounting said receptacle on a supporting object; and
a disposable needle receiving block positioned within and substantially filling said case, said block being sufficiently small to be inserted into said case through said first open end and being larger than said second open end whereby it is retained thereadjacent.

2. The parenteral needle receptacle of claim 1 wherein said base includes a raised portion or platform approximating the size and shape of said first open end whereby said case is releasably mounted on said base through a force fit between said walls and said platform.

3. The parenteral needle receptacle of claim 2 wherein said second open end is defined by a continuous ridge extending inwardly from said walls.

4. The parenteral needle receptacle of claim 3 wherein said block is generally cube-shaped and said case is generally cube-shaped.

5. The parenteral needle receptacle of claim 1 wherein said base includes an elevated platform having at least two slots extending therethrough, said receptacle further comprising at least two flexible, barbed members extending downwardly from said case through said slots and releasably engaging the underside of said platform opposite said block whereby said case is releasably mounted on said base.

6. The parenteral needle receptacle of claim 5 wherein said second open end is defined by a continuous ridge extending inwardly from said walls.

7. The parenteral needle receptacle of claim 6 wherein said block is generally cube-shaped and said case is generally cube-shaped.

8. The parenteral needle receptacle of claim 1 wherein said mounting means comprises adhesive tape having first and second adhesive sides, one of said sides being adhesively secured to said receptacle.

9. The parenteral needle receptacle of claim 1 wherein said attaching means comprises at least one magnet encapsulated within said receptacle.

10. The parenteral needle receptacle of claim 1 wherein said attaching means comprises at least one magnet supported by said base.

11. A parenteral needle receptacle comprising:
a base;
a case releasably mounted on said base, said case having walls defining a first open end adjacent said base and a second open end opposite to and smaller than said first open end, said second open end being defined by a shoulder extending inwardly from said walls, said base including a raised portion or platform approximating the size and shape of said first open end whereby said case is releasably mounted on said base through a force fit between said walls and said platform;
a disposable needle-receiving block positioned within and substantially filling said case, said block being sufficiently small to be inserted into said case through said first open end and sufficiently large that it will not pass through said second open end, whereby said block is entrapped between said base and said shoulder; and
means connected to said receptacle for attaching said receptacle to an object.

12. The parenteral needle receptacle of claim 11 wherein said attaching means comprises at least one magnet encapsulated within said base.

13. The parenteral needle receptacle of claim 11 wherein said attaching means comprises at least one magnet mounted on the underside of said platform opposite said block.

14. The parenteral needle receptacle of claim 11 wherein said attaching means comprises adhesive tape having first and second adhesive sides, one of said sides being adhesively secured to said receptacle.

15. A method of disposing of a used parenteral needle withdrawn from a patient comprising:
mounting a needle receptacle on an object proximate said patient, said receptacle including a case defining a void and an opening communicating with said void, said receptacle further comprising a needle-receiving block removably positioned within said void and accessible through said opening;
inserting said used parenteral needle through said opening into said block whereby said needle is protectively enclosed within said receptacle;
at a convenient time subsequent to said inserting step, removing said block and needle inserted therein from said case; and safely disposing of said block and said needle.

16. A method as defined in claim 15 wherein said receptacle comprises magnetic means; and wherein said mounting step comprises magnetically securing said receptacle to a ferrous object.

17. A method as defined in claim 15 wherein said receptacle comprises adhesive means; and wherein said mounting step comprises adhesively securing said receptacle to said object.

* * * * *